United States Patent
Hirao et al.

(10) Patent No.: US 7,511,172 B2
(45) Date of Patent: Mar. 31, 2009

(54) METHOD FOR PRODUCTION OF (METH)ACRYLIC ACID

(75) Inventors: Harunori Hirao, Himeji (JP); Kouji Ueno, Himeji (JP); Naoki Serata, Himeji (JP); Takeshi Yokogoshiya, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/880,549

(22) Filed: Jul. 23, 2007

(65) Prior Publication Data
US 2007/0270611 A1   Nov. 22, 2007

Related U.S. Application Data

(62) Division of application No. 10/859,036, filed on Jun. 2, 2004, now Pat. No. 7,332,626.

(30) Foreign Application Priority Data
Jun. 5, 2003   (JP) ............................. 2003-160767

(51) Int. Cl.
*C07C 51/16* (2006.01)

(52) U.S. Cl. .................................................. 562/532

(58) Field of Classification Search .................. None
See application file for complete search history.

(56) References Cited

U.S. PATENT DOCUMENTS

| 4,554,054 | A |   | 11/1985 | Coyle et al. |
| 4,618,709 | A |   | 10/1986 | Sada et al. |
| 5,087,744 | A |   | 2/1992  | Krabetz et al. |
| 5,198,578 | A | * | 3/1993  | Etzkorn et al. ............ 562/532 |
| 5,315,037 | A |   | 5/1994  | Sakamoto et al. |
| 5,817,865 | A |   | 10/1998 | Machhammer et al. |
| 6,051,736 | A |   | 4/2000  | Schraut et al. |
| 6,320,075 | B1 |  | 11/2001 | Ruedinger et al. |
| 6,482,981 | B2 |  | 11/2002 | Ueno et al. |
| 6,540,881 | B1 |  | 4/2003  | Sakamoto et al. |
| 6,599,397 | B2 |  | 7/2003  | Sakamoto et al. |
| 6,713,648 | B2 |  | 3/2004  | Hirao et al. |
| 2001/0003783 | A1 | | 6/2001 | Nishimura et al. |

(Continued)

FOREIGN PATENT DOCUMENTS

EP   0 495 504   1/1992

(Continued)

OTHER PUBLICATIONS

Notice of Reason for Rejection in Corresponding Japanese Patent Application No. 2003-160767 dated Apr. 25, 2007.

*Primary Examiner*—Karl J Puttlitz
(74) *Attorney, Agent, or Firm*—Mathews, Shepherd, McKay & Bruneau, P.A.

(57) ABSTRACT

A method for producing acrylic acid by absorbing acrylic acid at a high ratio and obtaining an acrylic acid-containing solution of high concentration is provided. This method comprises a step of circulating part of a discharged gas from an absorption step of acrylic acid to the reactor and discarding the remainder to the out side of system while the gas is cooled before circulation to the reactor. By the method, the acrylic acid-containing solution of high concentration is obtained due to decrease of an acrylic acid loss.

3 Claims, 1 Drawing Sheet

U.S. PATENT DOCUMENTS

2003/0120112 A1  6/2003  Hirao
2004/0063998 A1  4/2004  Hirao et al.

FOREIGN PATENT DOCUMENTS

| | | |
|---|---|---|
| EP | 0 990 636 | 2/1999 |
| EP | 1 388 532 | 2/2004 |
| EP | 1 388 533 | 2/2004 |
| GB | 2 004 886 | 9/1978 |
| GB | 2 045 759 | 3/1980 |
| GB | 2 146 636 | 4/1985 |
| JP | 52 108 917 A1 | 9/1977 |

* cited by examiner

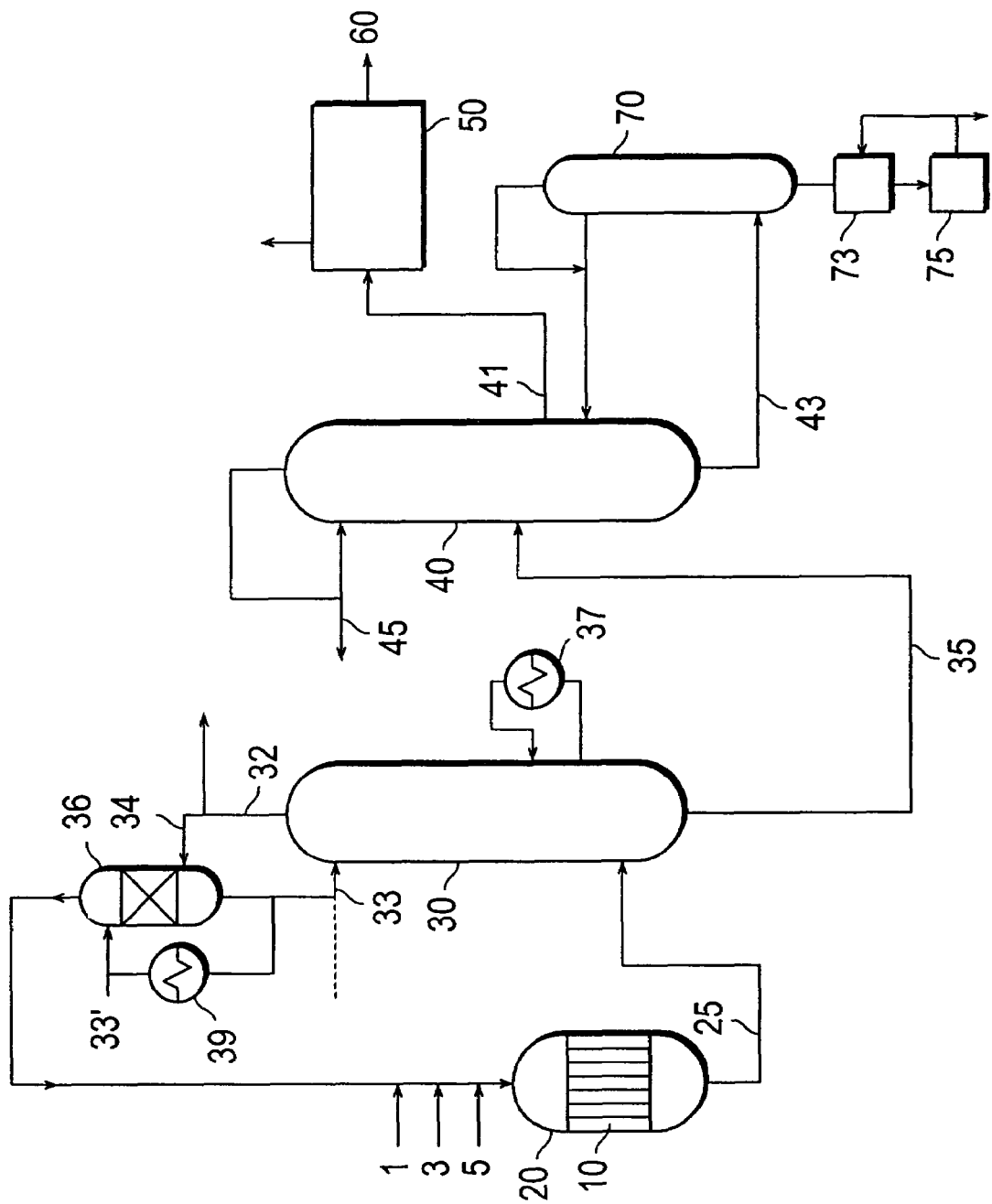
FIGURE

METHOD FOR PRODUCTION OF (METH)ACRYLIC ACID

CROSS-REFERENCE TO RELATED APPLICATION

This application is a divisional of U.S. patent application Ser. No. 10/859,036 filed Jun. 2, 2004 now U.S. Pat. No. 7,332,626, hereby incorporated in its entirety by reference into this application.

BACKGROUND OF THE INVENTION

1. Field of the Invention

This invention relates to a method for producing (meth) acrylic acid performing a step of discarding part of the exhaust gas of an absorption column and recycling the remainder to a reactor and a step of separating a condensable substance exclusively from the recycling gas, and/or a method for producing (meth)acrylic acid comprising a step of decreasing the water content entrained in a molecular oxygen-containing gas supplied to the reactor, thereby enhancing an absorption efficiency of (meth)acrylic acid.

2. Description of the Related Art

Commercial production of acrylic acid generally resorts to the method of propylene oxidation which consists in subjecting propylene and/or acrolein to catalytic gas phase oxidation. When acrylic acid is produced by this method of propylene oxidation, the step of propylene oxidation gives rise to such impurities as water, acids like propionic acid, acetic acid, and maleic acid, and aldehydes like acrolein, furfural, and formaldehyde and ketoses like acetone, in the form of by-products. The gas containing these by-products is absorbed as an acrylic acid-containing solution generally via contact with an absorption solvent. This solution is subsequently purified by separating the absorption solvent by such a means as distillation and further separating low boiling substances and high boiling substances. The minute amount of such impurities as aldehydes which cannot be easily separated by distillation is possibly purified by a chemical treatment or a process of crystallization. The purification to a high degree necessitates many steps and complicates equipment and operation and forms one cause for degrading the yield of acrylic acid.

One known method, for example, produces acrylic acid of high purity by absorbing an acrylic acid-containing gas resulting from catalytic gas phase oxidation with a high boiling solvent, distilling the solvent now entraining the gas thereby separating it into the solvent and crude acrylic acid, and subsequently subjecting the crude acrylic acid to a process of crystallization (JP-A-1997-227445). This method, however, forms a complicated procedure which comprises a step of cooling an acrylic acid-containing gas with a venturi, then subjecting the cooled gas to a step of absorption and subsequently to a step of removing low boiling substances, thereafter a step of separating the residue in a distillation column into a high boiling substance and a medium boiling substance, and a step of extracting crude acrylic acid from the intermediate stage of the column.

If an acrylic acid solution having a high concentration is successfully treated at the step of acrylic acid production, this treatment will prove efficient in allowing a decrease in the amount of treatment at the subsequent purifying step. Thus, a method has been proposed which comprises supplying a reaction composition containing more than 7 vol % of propylene, molecular oxygen, steam, and the balance of an inert gas to a reactor having disposed therein numerous reaction tubes each packed with a catalyst and furnished with two reaction zones thereby allowing utility of a propylene reactant of a high concentration (JP-A-2000-103761). In one example 1 cited in this official gazette, the absorption with water obtained an acrylic acid solution having an average concentration of 69.5 wt %.

Another method has been disclosed which comprises introducing an acrylic acid-containing gas into the absorption column, introducing a recovery water containing acetic acid emanating from the bottom liquid of a solvent recovering column at the purifying step into the top of the absorption column thereby effecting absorption of acrylic acid therein, and producing as the bottom liquid of the absorption column an acrylic acid-containing solution composed of 50-80 wt % of acrylic acid, 2-5 wt % of acetic acid, and the balance of water (JP-A-1993-246941). This method obtains purified acrylic acid by subjecting the acrylic acid-containing solution to azeotropic dehydration using a mixed solution of two or more azeotropic solvents and subsequently passing the product of dehydration through such steps as the removal of high boiling substance.

Still another method has been disclosed which, in the absorption with water of an acrylic acid-containing gas resulting from a reaction of catalytic gas phase oxidation, comprises supplying the recovery water emanating from the step of azeotropic dehydration to the absorption column, supplying the resultant acrylic acid-containing solution to a stripping column, and obtaining an acrylic acid solution composed of 70.9 wt. % of acrylic acid, 25.6 wt. % of water, and 2.0 wt. % of acetic acid via the bottom of the stripping column (JP-A-2001-199931). This method obtains purified acrylic acid by performing azeotropic dehydration of the acrylic acid-containing solution and subsequently subjecting the product of dehydration to the step of crystallization.

The methods published in the official gazettes mentioned above, however, necessitate a stripping column for the purpose of obtaining an aqueous solution containing acrylic acid at a high concentration and, when an organic solvent is used as an absorption solvent, subsequently necessitate a step of solvent separation. Further, they have such a complicated procedure as adjusting anew the conditions of the reaction of catalytic gas phase oxidation. In spite of these measures, the acrylic acid-containing solutions they produce have concentrations which hardly deserve to be called fully satisfactory. In JP-A-1997-117445 mentioned above, for example, since the high boiling solvent used therein has a lower absorbing power than water, the acrylic acid concentration of the solution obtained at the step of absorption is about 20 wt. % at the most.

When the acrylic acid concentration is low in the acrylic acid-containing solution obtained from the step of absorption, this low concentration results in adding to the impurities to be separated at the subsequent steps and requiring the equipment for the separation to be enlarged and inevitably entailing an increase in the amount of necessary utilities. An attempt to heighten the acrylic acid concentration in the acrylic acid-containing solution obtained at the step of absorption is actually infeasible commercially because it increases the loss of acrylic acid at the step of absorption. In the inventions of JP-A-2000-103761, JP-A-1993-246941, and JP-A-2001-199931, the acrylic acid concentrations in the solutions obtained at the step of absorption are 80 wt. % at the most and the losses of acrylic acid, therefore, are presumed to be high.

SUMMARY OF THE INVENTION

The acrylic acid-containing solution in the absorption column is decided by the amount of acrylic acid and the amount of a solvent to be supplied therein. To prepare the acrylic acid-containing solution of a high concentration, therefore, it suffices to lower the amount of the solvent. An attempt to obtain bottom liquid which have an acrylic acid concentration of not less than 70 wt. %, however, is not easily carried out because the loss of acrylic acid through the top of the absorption column increases when the amount of the solvent for absorbing acrylic acid supplying to the absorption column is decreased. The present inventors have pursued a study in search of conditions which permit preparation of an acrylic acid-containing solution of high concentration while lowering the loss of acrylic acid. They have perfected this invention as a result. Specifically, they have found that when the amount of the water contained in the raw material is decreased, the amount of the water introduced into the reactor can be decreased and the (meth)acrylic acid solution of high concentration is obtained while the loss of (meth)acrylic acid is allayed, and that while part of the gas emanating from the absorption column is recycled to the reactor, the (meth) acrylic acid solution of high concentration is obtained as suppressing the loss of (meth)acrylic acid by decreasing the amount of a condensable substance in the recycled gas being introduced via the reactor in the form of a gas again into the absorption column excluding no change in the amount of the condensable substance in the waste gas discharged from the system. This invention has been perfected based on this knowledge.

This invention, in a method for producing (meth)acrylic acid by a procedure comprising a step of catalytic gas phase oxidation of the raw material of (meth)acrylic acid, a step of absorbing (meth)acrylic acid, and a step of circulating part of the gas discharged from the absorbing step as a recycle gas to a reactor and discarding the remainder of the discharged gas as a waste gas to the out side of system, intends not to decrease a condensable substance exclusively from the waste gas to the out side of system but from the recycle gas, and obtaining a (meth)acrylic acid solution of high concentration at the absorbing step. The loss of acrylic acid is allayed, namely the absorption efficiency of acrylic acid is enhanced. Further, the deterioration of the catalyst due to the acid can be prevented because the content of acid components in the recycle gas is also decreased. Since the decrease of the consensable substance is effected exclusively in the recycle gas, the cost of equipment and the cost of utilities for decreasing the consensable substance can be repressed.

This invention is also directed toward providing a method for producing (meth)acrylic acid by a procedure comprising a step of supplying the raw material of (meth)acrylic acid and a molecular oxygen-containing gas to a reactor for catalytic gas phase oxidation thereby obtaining a (meth)acrylic acid-containing gas and a step of absorbing (meth)acrylic acid contained in the gas, characterized by removing the water contained in the molecular oxygen-containing gas prior to the introduction of the gas into the reactor. The use of the molecular oxygen-containing gas which has been dehumidified in advance results in decreasing the amount of water introduced into the reactor and permitting absorption of the (meth) acrylic acid of high concentration at a high yield.

This invention is further directed toward providing an apparatus for production of (meth)acrylic acid which comprises a reactor for catalytic gas phase oxidation reaction of raw material of (meth)acrylic acid, an absorption column for absorbing (meth)acrylic acid from the catalytic gas phase oxidation, and a piping for discharging a residual gas from the top of the absorption column after the absorption and circulating the gas as a recycle gas to the reactor and produces (meth)acrylic acid, wherein the piping is provided with a branch for expelling part of the discarded gas as a waste gas to the out side of system and a device for removing a condensable substance contained in the recycle gas is interposed between the branch and the reactor. This invention further provides an apparatus for production of (meth)acrylic acid which comprises an input line for introducing the raw material of (meth)acrylic acid and a molecular oxygen-containing gas into a reactor, the reactor for catalytic gas phase oxidation connected to the line, and the absorption column for absorbing (meth)acrylic acid resulting from the catalytic gas phase oxidation, wherein the inlet for the molecular oxygen-containing gas is furnished with a device for the removal of water.

According to this invention, by cooling exclusively part of the gas discharged from the (meth)acrylic acid absorption column as circulating a part of the discharged gas to the reactor, it is made possible to decrease the amount of water contained in the recycle gas and enhance the absorption efficiency of (meth)acrylic acid. Further, by decreasing the acid content in the recycle gas, it is made possible to prevent the catalyst from deterioration.

The decrease of the water content is also attained by dehumidifying the air to be supplied to the reactor in advance of the supply. Consequently, the absorption efficiency of (meth) acrylic acid can be enhanced as well.

According to this invention, the (meth)acrylic acid-containing solution can be obtained in high concentration. As a result, the contained water can be removed in the subsequent step without requiring use of an azeotropic solvent and the step of azeotropic dehydration can be omitted and, owing to the absence of survival of the azeotropic solvent, the step of separation of the solvent can be eliminated, with the result that the process of production will be simplified. Now, the invention will be described in detail below.

BRIEF DESCRIPTION OF THE DRAWING

FIGURE is a process diagram illustrating one example of the preferred mode of embodying this invention.

DESCRIPTION OF THE PREFERRED EMBODIMENT

The first aspect of this invention is directed toward providing a method for producing (meth)acrylic acid by a procedure comprising a step of subjecting raw material of (meth)acrylic acid to a reaction of catalytic gas phase oxidation, a step of absorbing (meth)acrylic acid, and a step of circulating part of a gas discharged from the absorbing step as a recycle gas to a reactor and discarding the remainder of the discharged gas as waste gas to the out side of system, wherein the concentration of a condensable substance contained in the recycle gas is lower than the concentration of a condensable substance contained in the waste gas (i), and a method for producing (meth) acrylic acid by a procedure comprising a step of supplying the raw material of (meth)acrylic acid and a molecular oxygen-containing gas to a reactor for the reaction of catalytic gas phase oxidation thereby obtaining a (meth)acrylic acid-containing gas and a step of absorbing (meth)acrylic acid contained in said gas, wherein said molecular oxygen-containing gas is introduced into said reactor after the water component contained in said gas has been removed (ii).

For the purpose of obtaining a (meth)acrylic acid-containing solution of high concentration, it is necessary either to decrease the amount of water introduced into the system or to increase the amount of water discarded to the out side of system. Heretofore, it has been customary to recycle the gas discharged from the absorption column to the reactor without cooling the gas in the meantime. The present invention obtains the (meth)acrylic acid solution of high concentration by cooling the recycle gas thereby decreasing the amount of water contained therein and consequently decreasing the amount of water recycled to the reactor and/or by dehumidifying the air supplied as an oxidizing gas to the reactor prior to the supply to the reactor thereby decreasing the amount of water introduced into the absorption column. When the whole amount of the discharged gas from the absorption column is cooled and the amount of water discarded to the out side of system is consequently decreased, the amount of water in the recycle gas is indeed decreased but the absorption efficiency of (meth)acrylic acid is not heightened and rather lowered widely than when the cooling is omitted. This invention, therefore, effects condensation of not merely the water component but also the acid component in the part of the gas discharged from the (meth)acrylic acid absorption column which is recycled as the so-called recycle gas to the reactor to enhance the absorption efficiency of (meth)acrylic acid and further prevent the catalyst from deterioration. The decrease of the concentration of a condensable substance contained in the recycle gas (i) and the removal of the water component from the air mentioned above (ii) may be carried out either singly or in combination.

As used in this specification, the term "(meth)acrylic acid" refers to acrylic acid or methacrylic acid and the term "condensable substance" to a substance which assumes a liquid state at 20° C. under an atmospheric pressure. Now, one example of the preferred embodiment this invention in the production of acrylic acid from propylene and/or acrolein as the raw material gas will be described below based on The FIGURE.

First, such a molecular oxygen-containing gas as air 3 having the amount of water decreased with a dehumidifying device not shown in the diagram, the raw material of acrylic acid such as propylene and/or acrolein 1, and a diluting gas 5 are mixed together. At this step, a recycle gas 34 which has undergone the acrylic acid absorbing step and subsequently discharged through the top of the absorption column may be mixed with the air, propylene and/or acrolein, and diluting gas. In this case, the recycle gas 34 may be used as a diluting gas. This mixed gas (hereinafter referred to occasionally as "the raw material gas") is supplied to a reactor 20 packed with a catalyst 10 for catalytic gas phase oxidation and subjected therein to a reaction of catalytic gas phase oxidation to obtain an acrylic acid-containing gas 25. The gas 25 is supplied to the absorption column 30 via the bottom thereof and an aqueous solution absorbent 33 is supplied to the absorption column 30 via the top thereof, with the result that the acrylic acid-containing gas 25 and the aqueous solution absorbent 33 will be brought into mutual contact. In this specification, the part of a discharged gas 32 from the top of the absorption column 30, namely the discharge gas circulated to the reactor will be referred to as "a recycle gas" and the part thereof, namely the gas discharged to the out side of system will be referred to as "a waste gas." In this invention, the recycle gas 34 alone is introduced into a cooling column 36, cooled therein by gas-liquid contact with an absorbing water 33' newly supplied into the system, condensed a condensable substance contained in the recycle gas, and subsequently circulated to the reactor 20. The resultant condensed liquid may be mixed with the absorbing water 33' mentioned above and supplied as the aqueous solution absorbent 33 to the absorption column 30. Thus, by adjusting the temperature of the top of the absorption column with a cooling device 37 disposed in the absorption column, it is made possible to obtain a solution 35 containing acrylic acid in high concentration via the bottom of the absorption column.

The steps following the absorbing step do not need to be particularly restricted. For the sake of efficiently purifying the acrylic acid-containing solution of high concentration, this invention contemplates a procedure which comprises supplying the acrylic acid-containing solution 35 to a first distillation column 40 and causing a low boiling substance contained therein to remove and consequently obtaining crude acrylic acid 41. Acrylic acid 60 as a finished product is obtained by supplying the crude acrylic acid 41 to a crystallizing column 50. The bottom liquid of the absorption column, depending on the composition thereof, may be directly supplied to the crystallizing column 50 without using the first distillation column 40. Since the high boiling substance contained in the bottom liquid 43 of the first distillation column 40 contains acrylic acid dimer, the bottom liquid is supplied to a second distillation column 70 furnished on the bottom thereof with a thin film distilling device 73 so as to concentrate the acrylic acid dimer. Subsequently, the dimer is retained in a dimmer decomposing tank 75 so as to be thermally decomposed into acrylic acid. This acrylic acid may be circulated via the second distillation column 70 to the first distillation column 40 and/or the absorption column 30 so as to be recovered as the finished product. The term "low boiling substance" refers to a substance which has a lower boiling point than (meth)acrylic acid in the normal state and the term "high boiling substance" refers to a substance which has a higher boiling point than (meth)acrylic acid in the normal state.

In this invention, propylene and/or acrolein can be used as the raw material gas of acrylic acid. While the reactor 20 does not need to be particularly restricted but is only required to be capable of performing a reaction of catalytic gas phase oxidation. The shell-and-tube type reactor can be used advantageously in respect that it excels in the efficiency of reaction. By packing the reactor 20 with the well-known catalyst 10 for catalytic gas phase oxidation and then bringing the raw material gas into contact with such a molecular oxygen-containing gas as oxygen or air, it is made possible to effect the oxidation of the raw material gas. When propylene is used as the raw material gas, the propylene concentration is in the range of 7-15 vol % and the molecular oxygen concentration is such that the ratio of propylene:molecular oxygen (by volume) falls in the range of 1:1.0-2.0. Air may be used as the source of supply of molecular oxygen. When the air contains a water component, it is preferred to be dehumidified prior to the supply thereof to the reactor. The dehumidification is preferred because it is capable of decreasing the amount of water introduced into the reactor and consequently decreasing the amount of water introduced to the absorption column. It is permissible to use an oxygen-enriched air or purified oxygen in the place of air. As concrete examples of the diluting gas 5, nitrogen, carbon dioxide, and other inert gases may be cited.

In this invention, the recycle gas may be introduced into the reactor after it has been cooled to induce condensation of a condensable substance. When the recycle gas is used in this manner, the recycle gas is deprived of the water component in advance so that the water concentration in the raw material gas supplied to the reactor falls in the range of 0-10 vol %, preferably in the range of 0-7 vol %, and particularly in the range of 0-6 vol %. When the molecular oxygen-containing gas is deprived of the water component without using the recycle gas, the concentration of the water component in the raw material gas supplied to the reactor is so adjusted as to fall in the range of 0-5 vol %, more preferably in the range of 0-3 vol %, and particularly preferably in the range of 0-1 vol %. If the concentration exceeds 10 vol %, the excess will possibly result in causing the water component supplied via the reactor to the absorption column to increase the acrylic acid loss ratio. The total acid concentration is so adjusted at to fall in the range of 0-0.2 vol % and more preferably in the range of 0-0.1 vol %. If the total acid concentration exceeds 0.2 vol %, the excess will possibly result in accelerating the deterioration of the catalyst by oxidation. The recycle gas contains unaltered propylene and acrolein, oxygen, diluting gas, etc. in addition to the water component and the acid component. The propylene, oxygen, water component concentration, and total acid concentration mentioned above can be easily adjusted by computing the amount of the water component contained in the recycle gas and the amount thereof to be incorporated in the raw material gas so as to enable the water component concentration and the total acid concentration in the raw material gas to fall in the optimum ranges mentioned above and computing the propylene concentration and the oxygen concentration in the recycle gas thereby deciding the amount of propylene and the amount of air to be newly supplied to the reactor. The term "total acid" as used herein refers to compounds having a carboxyl group. The recycle gas contains acrylic acid, formic acid, and acetic acid as compounds answering the description.

The reaction of catalytic gas phase oxidation performed by using propylene as the raw material is generally carried out in two stages by the use of two kinds of catalyst 10 for catalytic gas phase oxidation. The catalyst for the first stage of this reaction is capable of forming acrolein mainly by the gas phase oxidation of the raw material gas containing propylene in a gas phase and the catalyst for the second stage of the reaction is capable of forming acrylic acid mainly by the gas phase oxidation of the raw material containing acrolein. As the catalyst for the first stage of the reaction, a complex oxide containing iron, molybdenum, and bismuth may be cited. As the catalyst for the second stage of the reaction, a catalyst having vanadium as an essential component may be cited.

The FIGURE depicts the mode of performing the two-stage reaction mentioned above with a single reactor. Optionally, this reaction may be performed in a tandem system having two different reactors connected to each other. The acrylic acid-containing gas 25 which is obtained by the reaction of catalytic gas phase oxidation contains 5-14 vol % of acrylic acid, 0.1-2.5 vol % of acetic acid, 0.5-3 vol % of molecular oxygen, and 5-36 vol % of water and other components which are by-products of reaction such as the unaltered component of the raw material gas, propionic acid, maleic acid, acetone, acrolein, furfural, formaldehyde and $CO_x$.

In the acrylic acid absorption column 30, any of the known methods of contact may be used for establishing contact between the acrylic acid-containing gas and the aqueous solution absorbent. As concrete examples of such methods of contact, crossflow contact devices using a bubble-cap tray, a perforated tray, a jet tray, a valve tray; and counter current contact devices using a dual flow tray, a ripple tray, structured packings of gauze type, sheet type, and grid type and random packings may be cited.

As the aqueous solution absorbent 33 to be used in this invention, a wide variety of aqueous solutions which are capable of absorbing acrylic acid are available. The condensate resulting from cooling the recycle gas may be used as the aqueous solution absorbent. Since the condensate often contains acrylic acid, it is preferred to be reused as the aqueous solution absorbent. The temperature of the aqueous solution absorbent at the time of introduction falls in the range of 0-50° C. and preferably in the range of 10-40° C.

The flow rate ratio of mass of the absorbing water (which excludes the condensate from the recycle gas and corresponds to the absorbing water 33' shown in The FIGURE) to the acrylic acid-containing gas may be properly selected to suit the target acrylic acid concentration. The absorption of acrylic acid is effected by counter current contact using a mass flow rate of the absorbing water of 0.1-1.5 times, preferably 0.1-1.0 times, and particularly 0.15-0.8 times to the mass flow rate of acrylic acid contained in the acrylic acid-containing gas. If the mass flow rate ratio falls short of the level of 0.1 times, the shortage will possibly induce an extreme decrease of the efficiency of the acrylic acid absorption column. Conversely, if it exceeds the level of 1.5 times, the excess will render the acquisition of an acrylic acid-containing solution of high concentration difficult. Incidentally, the absorbing water may contain therein for the purpose of preventing such polymerizing substances as acrylic acid from succumbing to polymerization one or more compounds selected from the group consisting of N-oxyl compounds, phenol compounds, manganese salts such as manganese acetate, copper salts of dialkyl-dithiocarbamic acid such as copper dibutylthiocarbamate, nitroso compounds, amine compounds, and phenothiazine which are cited as in the official gazettes of JP-A-2001-348360, 2001-348358, and 2001-348359.

The acrylic acid absorption column is generally operated above normal pressure. In this invention, the column top pressure (gauge pressure) is set in the range of 0-0.4 MPa, preferably in the range of 0-0.1 MPa, and particularly in the range of 0-0.03 MPa. If this pressure falls short of 0 MPa (gauge pressure), the shortage will necessitate a pressure decreasing device and consequently add to the cost of equipment and the cost of utilities. Conversely, if the pressure exceeds 0.4 MPa (gauge pressure), the excess will possibly require the temperature of the absorption column to be elevated considerably for the purpose of discharging a low boiling substance from the column top and consequently degrade the absorption efficiency. The column top temperature falls generally in the range of 30-85° C. and particularly in the range of 40-80° C. In this invention, the acrylic acid-containing solution 35 comprising 70-98 wt. % of acrylic acid, 1-29 wt. % of water, and 1-10 wt. % of impurities (such as acids like acetic acid, maleic acid, and propionic acid, aldehydes like furfural and formaldehyde) is obtained under the conditions of absorption mentioned above.

This invention is characterized by the fact that when part of the gas discharged through the top of the absorption column 30 is recycled to the reactor 20 and the remainder thereof is discarded, the concentration of the condensable substance contained in the recycle gas is made lower than the concentration of the condensable substance contained in the waste gas. Water, acrylic acid, and acetic acid are condensable substances. The reason for decreasing their concentrations and consequently decreasing their amount for circulation to the absorption column resides in enhancing the absorption efficiency of acrylic acid. The gas discharged from the absorption column may be given any of such treatments as increase of pressure, elevation of temperature, and combustion before the gas is separated into the cycle gas and the waste gas. To lower the concentrations of such condensable substances, it is only necessary that the recycle gas alone be cooled so as to condense such condensable substances as water and acrylic acid, etc. and decrease the amount of the water component and the amount of acrylic acid, etc. When the discharged gas is cooled, the recycle gas must be cooler than the waste gas. This limitation is necessary because the concentrations of condensable substances could not be otherwise differentiated between the recycle gas and the waste gas. Specifically, as demonstrated in the working examples cited herein below, when the whole amount of the gas discharged from the absorption column is cooled to lower the concentrations of the condensable substances contained in the recycle gas, the acrylic acid loss ratio is rather suffered to increase to a greater level than when then the recycle gas is not cooled at all. Though this phenomenon remains yet to be clarified, it may be logically explained by a postulate that since the amount of the water component contained in the discharged gas is increased in accordance as the temperature of this gas is heightened, the cooling effected also on the waste gas possibly obstruct the efficient waste of the water component to the out side of system. In any event, when the whole amount of the discharged gas is cooled and reused in the absorption column, the efficiency of the absorption with the aqueous solution absorbent is degraded consequently. As a result, the concentration of acrylic acid in the gas discharged from the absorption column increases with the elapse of time, the amount of acrylic acid discarded as the waste gas from the system increases, and the acrylic acid loss ratio eventually increases. When part of the piping for circulating the gas discharged via the top of the absorption column as the recycle gas to the reactor is furnished with a branch for discarding the waste gas, therefore, it is advisable to interpose a cooling device between the branch and the reactor to cool exclusively the recycle gas.

The method for cooling the recycle gas does not need to be particularly restricted. It is only required to resort to a device which is capable of condensing the condensable substances contained in the recycle gas. As concrete examples of the device answering the description, the shell-and-tube type heat exchanger, fin tube type heat exchanger, air cooled heat exchanger, double pipe heat exchanger, coil type heat exchanger, direct contact type heat exchanger, and plate type heat exchanger may be cited. Since the condensate more often than not contains such polymerizable substances as acrylic acid, however, the method of cooling which resorts to the combination of the cooling column 36 and such a cooling device 39 as illustrated in The FIGURE is commendable in respect that it permits easy supply of a polymerization inhibitor.

The cooling temperature of the recycle gas does not need to be particularly restricted. The total amount of the raw material gas supplied to the reactor is so cooled till condensation that the concentration of the water component therein falls in the range of 0-10 vol %, preferably in the range of 0-7 vol %, and particularly in the range of 0-6 vol % and further the concentration of the total acid falls in the range of 0-0.2 vol %, preferably in the range of 0-0.1 vol %. When air is used as the molecular oxygen-containing gas, the air contains a water component. The amount of the water component which exists after the recycle gas is cooled is computed from the amount of the air supplied, the aforementioned preferred concentration of the water component in the raw material gas and the amount of the raw material gas supplied and the cooling is carried out till the concentration of the water component found by the computation is reached. In this invention, the recycle gas is cooled to a temperature which is 1-50° C., preferably 2-40° C., and particularly preferably 3-30° C. lower than the temperature of the waste gas.

The condensate resulting from the condensation caused by cooling may be returned to the absorption column or may be withdrawn from the system instead of being so returned. Though the acrylic acid loss ratio is not changed very much between these two choices, the return to the absorption column is at an advantage in obviating the necessity for treating waste liquid. The recycle gas which has been cooled may be supplied without changing the temperature existing during the cooling to the reactor or may be heated with the object of preventing the deposition of acrylic acid on the inner wall of the piping extending from the cooling device to the reactor. In this invention, the method for decreasing the condensable substances in the recycle gas does not need to be limited to the cooling of the recycle gas.

In this invention, since the absorption column produces bottom liquid which have an extremely high acrylic acid concentration of 70-98 wt. %, the subsequent step of purification can be carried out easily. Though the method of purifying the acrylic acid-containing solution to such a high concentration as mentioned above does not need to be restricted, the method which comprises removing such low boiling substances as water contained in the solution and subsequently purifying the remaining solution by crystallization may be cited. For example, the acrylic acid-containing solution 35 is supplied to the first distillation column 40 and crude acrylic acid containing substantially no water is separated as a bottom column flow and/or a side column flow.

The first distillation column 40 does not need to be particularly restricted but is only required to be capable of separating acrylic acid. A packed column, a plate column (tray column), etc. are available.

The first distillation column 40 can execute expected distillation under the conditions that enable such low boiling substances as water and acetic acid to be separated. This distillation does not require use of an azeotropic solvent. This is because the absorbing step produces an acrylic acid-containing solution of high concentration and, as a result, such low boiling substances as water and acetic acid which are contained in the solution are efficiently separated as a distillate from the top of the first distillation column 40 without using use of an azeotropic solvent. Since no azeotropic solvent is used, the distillate mentioned above can be used as an acetic acid-containing aqueous solution without requiring oil-water separation. The conditions of the distillation may be properly selected, depending on the concentration of acrylic acid in the acrylic acid-containing solution 35 to be introduced and the purity of the crude acrylic acid aimed at. Commendably, the column top pressure (absolute pressure) is set in the range of 20-400 hPa, preferably in the range of 30 hPa-300 hPa, and particularly in the range of 30-200 hPa. If this pressure falls short of 20 hPa (absolute pressure), the shortage will be at a disadvantage in requiring the column, condenser, and vacuum device to be enlarged and the cost of equipment to be unduly increased. Conversely, if the pressure exceeds 400 hPa (absolute pressure), the excess will be at a disadvantage in heightening the temperature inside the distillation column 40 and adding to the possibility of polymerization. The column top temperature falls generally in the range of 30-70° C. and particularly in the range of 40-60° C. Then, the column bottom temperature falls generally in the range of 70-120° C. and particularly in the range of 80-110° C. The distillation performed under these conditions produces crude acrylic acid containing substantially no water and having an acetic acid content in the range of 0-1.0 wt. % as a column side stream of the distillation column.

In this invention, the purification of this crude acrylic acid may be executed by utilizing a step of azeotropic dehydration, a step of separating low boiling substances subsequent to the dehydrating step mentioned above, a step of separating high boiling substances, and other steps of purification which are disclosed in the official gazettes of JP-A-2000-290221, 2001-226320, 2001-348360, and 2001-348358 in addition to a distillation column illustrated as the first distillation column 40 in The FIGURE. This invention, however, is characterized by preparing an acrylic acid-containing solution of high concentration and purifying this solution and, as a result, enabling such low boiling substances as water and acetic acid to be removed from the solution without requiring use of an azeotropic solvent and avoiding installation of a solvent recovering column and an oil-water separating device for separating a solvent and a recovered water. Incidentally, the step of purifying acrylic acid does not need to be limited to purification by distillation. Optionally, the purification of acrylic acid may be effected by properly combining stripping, crystallization, extraction, absorption, and partial condensation.

This invention obtains the purified acrylic acid 60 by supplying the crude acrylic acid 41 to the crystallizing column 50. The crystallization is an operation for precipitating crystals from the liquid phase and the gas phase. This mode of operation can be performed by following the procedure disclosed in JP-A-2001-199931 with necessary modifications.

The bottom liquid of the second distillation column 70 have high viscosity. The distillation column 70, therefore, is preferred to be provided additionally on the column bottom side with the thin layer evaporator 73. Commendably, the second distillation column 70 executes the expected distillation with a number of theoretical plate in the range of 1-5 under a reduced pressure in the range of 10-150 hPa (absolute pressure) at a column bottom temperature of not higher than 120° C. The high boiling substances contained in the bottom liquid of the first distillation column 40 include acrylic acid dimer, maleic acid, and polymerization inhibitor, for example.

In this invention, acrylic acid may be distilled from the top of the second distillation column and part of the distillate may be supplied to any of the crystallizing device 50, the first distillation column 40, and the absorption column 30.

The liquid formed in the thin layer evaporator 73 mentioned above is supplied to the dimmer decomposing tank 75. In this dimmer decomposing tank 75, the acrylic acid dimer is decomposed at a temperature in the range of 120-220° C. The hold up time (the liquid amount in of the dimmer decomposing tank/amount of waste oil), though variable with the temperature of thermal decomposition, generally falls in the range of 20-50 hours. After the acrylic acid dimer is decomposed into acrylic acid, the acrylic acid can be effectively utilized by circulating the acrylic acid to the thin layer evaporator 73 and supplying the distillate from the top of the second distillation column to the first distillation column 40. In this invention, the acrylic acid-containing solution of high concentration can be prepared in the acrylic acid absorption column 30, which solution can be prevented from polymerization by the addition of a polymerization inhibitor. At the step of absorption and the step of purification, polymerization inhibitors conforming to relevant acrylic acid concentrations are used. In this invention, these polymerization inhibitors are expelled out of the system as a waste liquid of the dimmer decomposing tank 75 to allow manufacture of acrylic acid 60 of high concentration as a finished product.

Incidentally, the residual mother liquid recovered from the crystallizing device 50 may be supplied in the whole amount to any of the absorption column 30, the first distillation column 40, the second distillation column 70, the thin layer evaporator 73, and the dimmer decomposing tank 75. Otherwise, part of the mother liquid may be discharged as waste oil to the out side of system. When the whole amount of the residual liquid mentioned above is supplied to the acrylic acid dimer decomposing step, part of the acrylic acid recovered from the acrylic acid dimer decomposing step may be discharged to the out side of system for the purpose of avoiding concentration of low boiling substances. Otherwise, the acrylic acid may be subjected to a chemical pretreatment for the purpose of converting aldehydes and maleic acid to high boiling substances before it is supplied to the acrylic acid dimer decomposing step. As a result, the concentration of impurities in the acrylic acid to be recovered by the acrylic acid dimer decomposing step can be decreased. This mode of operation may be carried out by following the procedure disclosed in JP-A-2001-199931 with necessary modifications.

The method for producing acrylic acid has been described hitherto. Methacrylic acid may be produced by using at least one compound selected from the group consisting of methacrolein, isobutyl aldehyde, isobutyric acid, and isobutane in the place of propylene and/or acrolein and also using a catalyst containing at least the oxides of phosphorus, molybdenum, vanadium, iron, copper, and antimony and used for the production of methacrylic acid as disclosed in JP-A-1987-161739, a catalyst containing at least the oxides of phosphorus and molybdenum and used for the production of methacrylic acid as disclosed in JP-A-1992-90853, a multicomponent type catalyst containing phosphorus, molybdenum, vanadium, and copper and used for the production of methacrylic acid as disclosed in JP-A-1993-96172, a catalyst containing at least the oxides of phosphorus, molybdenum, vanadium, and arsenic and used for the production of methacrylic acid as disclosed in JP-A-1994-86932, or a catalyst containing at least the oxides of molybdenum, phosphorus, vanadium, antimony, rhenium and used for the production of methacrylic acid as disclosed in JP-A-1995-163883. The purification of a methacrylic acid-containing solution having a concentration in the range of 70-95 wt. % may be effected by following the process illustrated in The FIGURE with necessary modification or by adopting the hitherto known method for the production of methacrylic acid.

The second aspect of this invention is directed toward an apparatus for the production of (meth)acrylic acid, comprising a reactor for subjecting the raw material of (meth)acrylic acid to catalytic gas phase oxidation, a (meth)acrylic acid absorption column for absorbing (meth)acrylic acid obtained by the catalytic gas phase oxidation, and a piping for discharging residual gas from the top of the absorption column and circulating the discharged gas as a recycle gas to the reactor, wherein the piping is furnished with a branch for discarding part of the waste gas to the out side of system and a device for removing condensable substances contained in the recycle gas is interposed between the branch and the reactor.

The use of this apparatus enables the condensable substances exclusively in the part of the discharged gas from the absorption column which is recycled to the reactor to remove or decrease and consequently allows the amounts of water, acrylic acid, and acetic acid contained in the recycle gas to decrease. As a result, the absorption efficiency of (meth)acrylic acid can be exalted. Further, the catalyst can be prevented from deterioration because the amounts of acid component contained in the recycle gas to the reactor are decreased.

As a means to remove such condensable substances, a device for cooling a gas is available. As concrete examples of the gas cooling device, the combination of a cooling column and a cooling device illustrated in The FIGURE and the shell-and-tube heat exchanger, fin tube type heat exchanger, air-cooled type heat exchanger, double pipe type heat exchanger, coil type heat exchanger, direct contact type heat exchanger, and plate type heat exchanger enumerated above may be cited.

The third aspect of this invention is directed to an apparatus for the production of (meth)acrylic acid, comprising an introduction line for introducing the raw material of (meth)acrylic acid and a molecular oxygen-containing gas to a reactor, the reactor used for catalytic gas phase oxidation and connected to the line, and a (meth)acrylic acid absorption column for absorbing the (meth)acrylic acid obtained by the catalytic gas phase oxidation, wherein the molecular oxygen-containing gas introducing line is furnished with a device for removing a water component.

The reaction of catalytic gas phase oxidation uses a molecular oxygen-containing gas. Air is used in most cases as the gas mentioned above. Generally, air contains a water component. When the apparatus is used even where air is supplied to the reactor, the water component contained in the air can be removed with the water component removing device before the air is introduced into the reactor. Thus, the amount of the water component supplied to the reactor can be decreased and the amount of the water component in the acrylic acid-containing gas introduced into the absorption column can be decreased as well. As a result, the absorption efficiency of acrylic acid can be exalted as described above and the acrylic acid-containing solution of high concentration can be manufactured. Moreover, according to the apparatus, the amount of acrylic acid discharged via the top of the absorption column can be decreased. When the discharged gas is recycled to the reactor, therefore, the deterioration of the catalyst with acids can be prevented because the amounts of acid components such as acrylic acid which are circulated to the reactor can be decreased.

As concrete examples of the water component removing device, various devices which are capable of effecting dehumidification by cooling, absorption, adsorption, and compression may be cited.

EXAMPLES

Now, this invention will be specifically described below with reference to working examples.

Example of Catalyst Production

A molybdenum-bismuth type catalyst was prepared by following the procedure of Example 1 cited in JP-A-2000-325795. This was labeled as "catalyst (I)." A molybdenum-vanadium type catalyst was prepared by following the procedure of example 1 cited in JP-A-1996-206504. This was labeled as "catalyst (II)."

(Formula of Calculation)

In the following working examples and comparative examples, the numerical values of the conversion of propylene, the yield of acrolein, the yield of acrylic acid, the recycle ratio, and the acrylic acid loss ratio were calculated in accordance with the following formulas.

Conversion of propylene(%)=[(Number of mols of propylene reacted)/(Number of mols of propylene supplied)]×100

Yield of acrolein (%)=[(Number of mols of acrolein formed)/(Number of mols of propylene supplied)]×100

Yield of acrylic acid(%)=[(Number of mols of acrylic acid formed)/(Number of mols of propylene supplied)]×100

Recycle ratio(%)=[(Number of mols of gas (before cooling) recycled to the reactor)/(Number of mols of gas discharged via the top of the absorption column)]×100

Acrylic acid loss ratio(%)=[(Amount of acrylic acid in waste gas and waste liquid)/(Amount of acrylic acid formed in the reactor)]×100

Example 1

Acrylic acid was produced by using the apparatus illustrated in The FIGURE.

A reactor furnished on the outer periphery thereof with a jacket for circulating a heat medium, containing therein reaction tubes 25 mm in inside diameter and 7,000 mm in length, and provided at a position of 3,500 mm from the lower part of the jacket with a perforated tube sheet dividing the heat medium jacket into two halves, an upper one and a lower one, was used. The lower part (the first reaction zone) and the upper part (the second reaction zone) of the reactor had their temperatures controlled by circulation of their respective heat media. The reactor was packed with (1) ceramic balls having an average diameter of 5 mm, (2) a mixture of catalyst (I) and ceramic balls of an average diameter of 5 mm at a volume ratio of 70:30, (3) catalyst (I), (4) raschig rings made of stainless steel and measuring 5 mm in outside diameter, 4.5 mm in inside diameter, and 6 mm in length, (5) a mixture of catalyst (II) and ceramic balls of an average diameter of 5 mm at a volume ratio of 75:25, and (6) catalyst (II) placed sequentially from the lower part toward the upper part of the reactor in respective bed lengths of 250 mm, 700 mm, 2,300 mm, 500 mm, 600 mm, and 1,900 mm.

To the first reaction zone of the reactor, propylene, air (the concentration of water component 2 wt. %), and part of the discharged gas (recycle gas) from the absorption column were circulated to supply 8.0 vol % of propylene, 14.4 vol % of $O_2$, and 5.0 vol % of $H_2O$ (the remainder comprising $N_2$, propane, COx, acrylic acid, and acetic acid, etc.) with the respective flow rates and the cooling temperature of the recycle gas so adjusted as to set the space velocity in the first reaction zone at 1,250 $hr^{-1}$ (STP).

The heat medium temperatures of the first reaction zone and the second reaction zone were so adjusted as to set the conversion of propylene at 97±0.5 mol % and the yield of acrolein at 1±0.5 mol % under the outlet pressure, 0.15 MPa (absolute pressure), of the second reaction zone to obtain an acrylic acid-containing gas.

The acrylic acid-containing gas thus obtained was introduced at a temperature of 170° C. into an acrylic acid absorption column having a number of theoretical plate of 23 found by calculation to absorb acrylic acid with water containing hydroquinone in an amount corresponding to 200 mass ppm relative to the amount of acrylic acid in the acrylic acid-containing gas introduced into the absorption column.

When the amount of the absorbing water was adjusted with the column top temperature of the acrylic acid absorption column set at 67° C. and the top pressure thereof set at 0.11 MPa (absolute pressure), the absorption column produced bottom liquid having an acrylic acid concentration of 90 wt. %.

The gas discharged via the top of the absorption column except the recycle gas was discharged as waste gas to the outside of system. The recycle gas was introduced into a cooling column to induce partial condensation of low boiling substances by cooling and then circulated to the reactor. The whole amount of the condensate and the absorbing water were mixed and returned to the absorption column. The cooling temperature was set at a level at which the $H_2O$ concentration in the first reaction zone reached the prescribed value.

Under the stabilized conditions acquired after the elapse of about 100 hours following the start of the reaction, the operation was analyzed to collect data. Consequently, the cooling temperature of the recycle gas was found to be 56.9° C., the recycle ratio 24.2%, the acid concentration at the inlet to the first reaction zone (the sum of the amounts of acrylic acid and acetic acid in mol ppm at the inlet to the first reaction zone) 150 ppm, and the yield of acrylic acid 86.8% and the acrylic acid loss ratio 2.80%. The outlined procedures of working examples and comparative examples and the results thereof are shown in Table 1 and Table 2.

Example 2

An operation was performed with the same apparatus under the same conditions as in Example 1 with the exception of adjusting the flow rates of relevant gases and the cooling temperature of the recycle gas so as to set the $H_2O$ concentration at the inlet of the first reaction zone at 2.5 vol % and adjusting the amount of the absorbing water so as to set the acrylic acid concentration in the bottom liquid of the absorption column at 90 wt. %.

Under the stabilized conditions acquired after the elapse of about 100 hours following the start of the reaction, the operation was analyzed to collect data. Consequently, the cooling temperature of the recycle gas was found to be 34.1° C., the recycle ratio 24.3%, the acid concentration at the inlet to the first reaction zone 30 ppm, the yield of acrylic acid 86.5% and the acrylic acid loss ratio 1.96%.

Example 3

An operation was performed with the same apparatus under the same conditions as in Example 1 with the exception of discarding the whole amount of the condensate formed by cooling and adjusting the amount of the absorbing water so as to set the acrylic acid concentration in the bottom liquid of the absorption column at 90 wt. %.

Under the stabilized conditions acquired after the elapse of about 100 hours following the start of the reaction, the operation was analyzed to collect data. Consequently, the cooling temperature of the recycle gas was found to be 56.9° C., the recycle ratio 24.2%, the acid concentration at the inlet to the first reaction zone 100 ppm, the yield of acrylic acid 86.9%, and the acrylic acid loss ratio 2.86%. Since the condensate was discarded, waste water occurred in an amount corresponding to 9 wt. % relative to the bottom liquid of the absorption column.

Comparative Example 1

An operation was performed with the same apparatus under the same conditions as in Example 1 with the exception of supplying the recycle gas to the first reaction zone without being cooled meanwhile, adjusting the relevant flow rates so as to set the concentrations of propylene and $O_2$ respectively at 8 vol % and 14.4 vol %, and adjusting the amount of the absorbing water so as to set the acrylic acid concentration in the bottom liquid of the absorption column at 90 wt. %. The concentration of $H_2O$ introduced into the first reaction zone was 7.0 vol %.

Under the stabilized conditions acquired after the elapse of about 100 hours following the start of the reaction, the operation was analyzed to collect data. Consequently, the recycle ratio was found to be 23.7%, the acid concentration at the inlet to the first reaction zone 1,130 ppm, the yield of acrylic acid 86.3%, and the acrylic acid loss ratio 3.52%.

Comparative Example 2

An operation was performed with the same apparatus under the same conditions as in Example 1 with the exception of changing the place of installation of the cooling device from the recycle gas line to the line for discharging the gas via the top of the absorption column, adjusting the flow rates of relevant gases and the cooling temperatures so as to set the concentrations of propylene, $O_2$, and $H_2O$ respectively at 8 vol %, 14.4 vol %, and 5.0 vol %, and adjusting the amount of the absorbing water so as to set the acrylic acid concentration in the bottom liquid of the absorption column at 90 wt. %.

Under the stabilized conditions acquired after the elapse of about 100 hours following the start of the reaction, the operation was analyzed to collect data. Consequently, the cooling temperature of the discharged gas from the top of the column was found to be 57.8° C., the recycle ratio 25.1%, the acid concentration at the inlet to the first reaction zone 2,420 ppm, the yield of acrylic acid 84.6%, and the acrylic acid loss ratio 8.91%.

Example 4

An operation was performed with the same apparatus under the same conditions as in Example 1 with the exception of changing the number of theoretical plate of the acrylic acid absorption column (found by calculation) to 10, setting the top temperature of the absorption column at 63° C., adjusting the relevant flow rates and the cooling temperatures so as to set the concentrations of propylene, $O_2$, and $H_2O$ respectively at 8 vol %, 14.4 vol %, and 4.0 vol %, and adjusting the amount of the absorbing water so as to set the acrylic acid concentration in the bottom liquid of the absorption column at 75 wt. %.

Under the stabilized conditions acquired after the elapse of about 100 hours following the start of the reaction, the operation was analyzed to collect data. Consequently, the cooling temperature of the recycle gas was found to be 50.2° C., the recycle ratio 25.2%, the acid concentration at the inlet to the first reaction zone 50 ppm, the yield of acrylic acid 86.7%, and the acrylic acid loss ratio 1.59%.

Comparative Example 3

An operation was performed under the same conditions as in Example 1 with the exception of using the same apparatus as in Example 4, supplying the recycle gas to the first reaction zone without being cooled meanwhile, adjusting the flow rates of relevant gases so as to set the concentrations of propylene and $O_2$ respectively at 8 vol % and 14.4 vol %, and adjusting the amount of the absorbing water so as to set the acrylic acid concentration in the bottom liquid of the absorption column at 75 wt. %. The concentration of $H_2O$ introduced into the first reaction zone was 6.2 vol %.

Under the stabilized conditions acquired after the elapse of about 100 hours following the start of the reaction, the operation was analyzed to collect data. Consequently, the recycle ratio was found to be 25.0%, the acid concentration at the inlet to the first reaction zone 460 ppm, the yield of acrylic acid 86.7%, and the acrylic acid loss ratio 1.93%.

Example 5

An operation was performed with the same apparatus under the same conditions as in Comparative Example 1 with the exception of disposing a dehumidifying device in the raw material air line to dehumidify the air introduced into the first reaction zone, supplying the recycle gas to the first reaction zone without being cooled meanwhile, adjusting the flow rates of relevant gases so as to set the concentrations of propylene and $O_2$ respectively at 8 vol % and 14.4 vol %, and adjusting the amount of the absorbing water so as to set the acrylic acid concentration in the bottom liquid of the absorption column at 90 wt. %. The concentration of $H_2O$ introduced into the first reaction zone was 6.5 vol %.

Under the stabilized conditions acquired after the elapse of about 100 hours following the start of the reaction, the operation was analyzed to collect data. Consequently, the recycle ratio was found to be 24.4%, the acid concentration at the inlet to the first reaction zone 960 ppm, the yield of acrylic acid 86.3%, and the acrylic acid loss ratio 2.95%.

Example 6

An operation was performed with the same apparatus under the same conditions as in Example 2 with the exception of disposing a dehumidifying device in the raw material air line to dehumidify the air introduced into the first reaction zone, cooling the recycle gas to the same temperature of 34.1° C. as in Example 2 and supplying the cooled recycle gas to the first reaction zone, adjusting the flow rates of relevant gases so as to set the concentrations of propylene, $O_2$, and $H_2O$ respectively at 8 vol %, 14.4. vol %, and 4.0 vol %, and adjusting the amount of the absorbing water so as to set the acrylic acid concentration in the bottom liquid of the absorption column at 90 wt. %. The concentration of $H_2O$ introduced into the first reaction zone at 18 vol %.

Under the stabilized conditions acquired after the elapse of about 100 hours following the start of the reaction, the operation was analyzed to collect data. Consequently, the recycle ratio was found to be 24.9%, the acid concentration at the inlet to the first reaction zone 20 ppm, the yield of acrylic acid 86.8%, and the acrylic acid loss ratio 1.70%.

TABLE 1

|  | Absorption column | | | Cooling column | | |
|---|---|---|---|---|---|---|
|  | Top temp. (° C.) | NTP | ACRYLIC ACID con. in bottom liquid | Object | Cooling temp. (° C.) | Condensate |
| Example 1 | 67 | 23 | 90 | Recycle gas | 56.9 | Recovered wholly |
| Example 2 | 67 | 23 | 90 | Recycle gas | 34.1 | Recovered wholly |
| Example 3 | 67 | 23 | 90 | Recycle gas | 56.9 | Discarded wholly |
| Com. Ex. 1 | 67 | 23 | 90 | No cooling | | — |
| Com. Ex. 2 | 67 | 23 | 90 | Whole gas | 57.8 | Recovered wholly |
| Example 4 | 63 | 10 | 75 | Recycle gas | 50.2 | Recovered wholly |
| Com. Ex. 3 | 63 | 10 | 75 | No cooling | | — |
| Example 5 | 67 | 23 | 90 | No cooling | | — |
| Example 6 | 67 | 23 | 90 | Recycle gas | 34.1 | Recovered wholly |

NTP: Number of theoretical plate

TABLE 2

|  | Air | inlet to reactor | | Results of acrylic acid | | |
|---|---|---|---|---|---|---|
|  | $H_2O$ (wt. %) | $H_2O$ (wt. %) | Acid (ppm) | Loss ratio | Yield | Recycle ratio |
| Example 1 | 2 | 5.0 | 150 | 2.80 | 86.8 | 24.2 |
| Example 2 | 2 | 2.5 | 30 | 1.96 | 86.5 | 24.3 |
| Example 3 | 2 | 5.0 | 100 | 2.86 | 86.9 | 24.2 |
| Com. Ex. 1 | 2 | 7.0 | 1130 | 3.52 | 86.3 | 23.7 |
| Com. Ex. 2 | 2 | 5.0 | 2420 | 8.91 | 84.6 | 25.1 |
| Example 4 | 2 | 4.0 | 50 | 1.59 | 86.7 | 25.2 |
| Com. Ex. 3 | 2 | 6.2 | 460 | 1.93 | 86.7 | 25.0 |
| Example 5 | 0.9 | 6.5 | 960 | 2.95 | 86.3 | 24.4 |
| Example 6 | 0.9 | 1.8 | 20 | 1.70 | 86.4 | 24.9 |

(Results)

(1) In working examples and comparative examples, the recycle ratios were invariably in the neighborhood of 25 vol % and the amounts of discarded gas showed no change. It is, therefore, evident that the variation of the acrylic acid loss ratio correlated with the concentrations of acrylic acid contained in the discarded gas.

(2) Comparison of Example 1 and Comparative Example 1 reveals that in Example 1, since the amount of a water component contained in the recycle gas was decreased by cooling the recycle gas, the acrylic acid loss ratio could be decreased when the acrylic acid-containing solution of a fixed concentration was prepared.

(3) Example 1 and Comparative Example 1 were equal in the top temperature of the absorption column, the number of theoretical plate, acrylic acid concentration in the absorption column, recycle gas cooling temperature, and amount of water component in the gas supplied to the reactor and were different in respect that the recycle gas was exclusively cooled in the former case and the discharged gas was wholly cooled in the latter case. Since the acrylic acid loss ratio was in proportion to the concentration of acrylic acid contained in the discharged gas from the absorption column as mentioned above, Comparative Example 2 produced higher acrylic acid concentrations in gas phase in both the acids at the inlet of the reactor and the discharged gas from the absorption column than Example 1. Since the acrylic acid concentrations of the bottom liquid of the absorption column were invariably 90 wt. %, the amount of acrylic acid not absorbed with the aqueous absorbent was large, namely the ratio of absorption of acrylic acid was low in Comparative Example 2. The ratio of reaction of acrylic acid was 86.8% in Example 1 and it was 84.6% in Comparative Example 1, indicating a decrease in the latter case. The cooling of the whole amount of the discharged gas from the absorption column resulted in changing the acid concentration at the inlet to the reactor and lowering the ratio of reaction of acrylic acid. Example 1 cooled the recycle gas exclusively and Comparative Example 1 cooled both the recycle gas and the waste gas. Thus, Example 1 enjoyed a decrease in the utilities required for cooling.

(4) Example 2 which decreased the amount of water component in the recycle gas by cooling the gas to a lower temperature than in Example 1 enjoyed a further decrease of the amount of water component introduced into the reactor and a further decrease of the acrylic acid loss ratio.

(5) Example 3 which did not circulate the condensate to the absorption column equaled Example 1 in the acrylic acid loss ratio and in the ratio of reaction of acrylic acid.

(6) Comparison of Example 4 which cooled the recycle gas and controlled the concentration of acrylic acid in the bottom liquid of the absorption column to 75 wt. % and Comparative Example 3 which did not cool the recycle gas reveals that Comparative Example 3 had a higher acrylic acid loss ratio than Example 4. The effect of this cooling on the acrylic acid loss ratio showed the same tendency to the effect of the presence or absence of the cooling of the recycle gas on the production of the acrylic acid of a concentration of 90 wt. % in the bottom liquid of the column.

(7) Example 5 which introduced the air dehumidified in advance with the object of lowering the amount of water component introduced into the first reaction zone attained the acrylic acid loss ratio lower than Comparative Example 1 which did not perform a treatment of dehumidification.

(8) Example 6 which cooled the recycle gas and introduced the air dehumidified in advance enjoyed the lowest concentration of acid at the inlet to the reactor and the lowest acrylic acid loss ratio in all the samples having an acrylic acid concentration of 90 wt. % in the bottom liquid of the column.

The invention claimed is:

1. A method for producing (meth)acrylic acid by a procedure comprising a step of supplying the raw material of (meth)acrylic acid and a molecular oxygen-containing gas to a reactor for the reaction of catalytic gas phase oxidation thereby obtaining a (meth)acrylic acid-containing gas and a step of absorbing (meth)acrylic acid contained in said gas, wherein said molecular oxygen-containing gas is introduced into said reactor after the water component contained in said gas has been removed and the water component concentration in raw material gas supplied to said reactor is in the range of 0-10 vol %.

2. A method according to claim 1, wherein the water component concentration in raw material gas supplied to said reactor is in the range of 0 to about 6.5 vol %.

3. A method according to claim 1, wherein the total acid concentration in raw material gas introduced into said reactor is in the range of 0-0.2 vol %.

* * * * *